United States Patent [19]

Nystrand

[11] B 3,994,486
[45] Nov. 30, 1976

[54] DIAPER FOLDING APPARATUS

[75] Inventor: Ernst Daniel Nystrand, Green Bay, Wis.

[73] Assignee: Paper Converting Machine Company, Green Bay, Wis.

[22] Filed: Oct. 21, 1974

[21] Appl. No.: 516,609

[44] Published under the second Trial Voluntary Protest Program on February 24, 1976 as document No. B 516,609.

Related U.S. Application Data

[63] Continuation-in-part of Ser. No. 404,037, Oct. 5, 1973, Pat. No. 3,860,004, which is a continuation-in-part of Ser. Nos. 297,750, Oct. 16, 1972, abandoned, and Ser. No. 373,247, June 25, 1973, abandoned.

[52] U.S. Cl. .................................. 270/62; 270/65; 270/93

[51] Int. Cl.² ........................................ B65H 45/00

[58] Field of Search ............................... 270/61–62, 270/86–94, 76–77, 69, 65; 93/84 R, 93 C, 13; 223/37–38

[56] References Cited

UNITED STATES PATENTS

| | | | |
|---|---|---|---|
| 2,114,124 | 4/1938 | Horton | 270/76 |
| 3,537,461 | 11/1970 | Imbert | 270/76 |

*Primary Examiner*—Edgar S. Burr
*Assistant Examiner*—A. Heinz
*Attorney, Agent, or Firm*—Tilton, Fallon, Lungmus, Chestnut & Hill

[57] ABSTRACT

A diaper folding apparatus employing an open frame drum equipped with a rapidly projecting tucker to force an intermediate diaper portion into a takeaway system and over aligned plates to develop leg folds.

5 Claims, 6 Drawing Figures

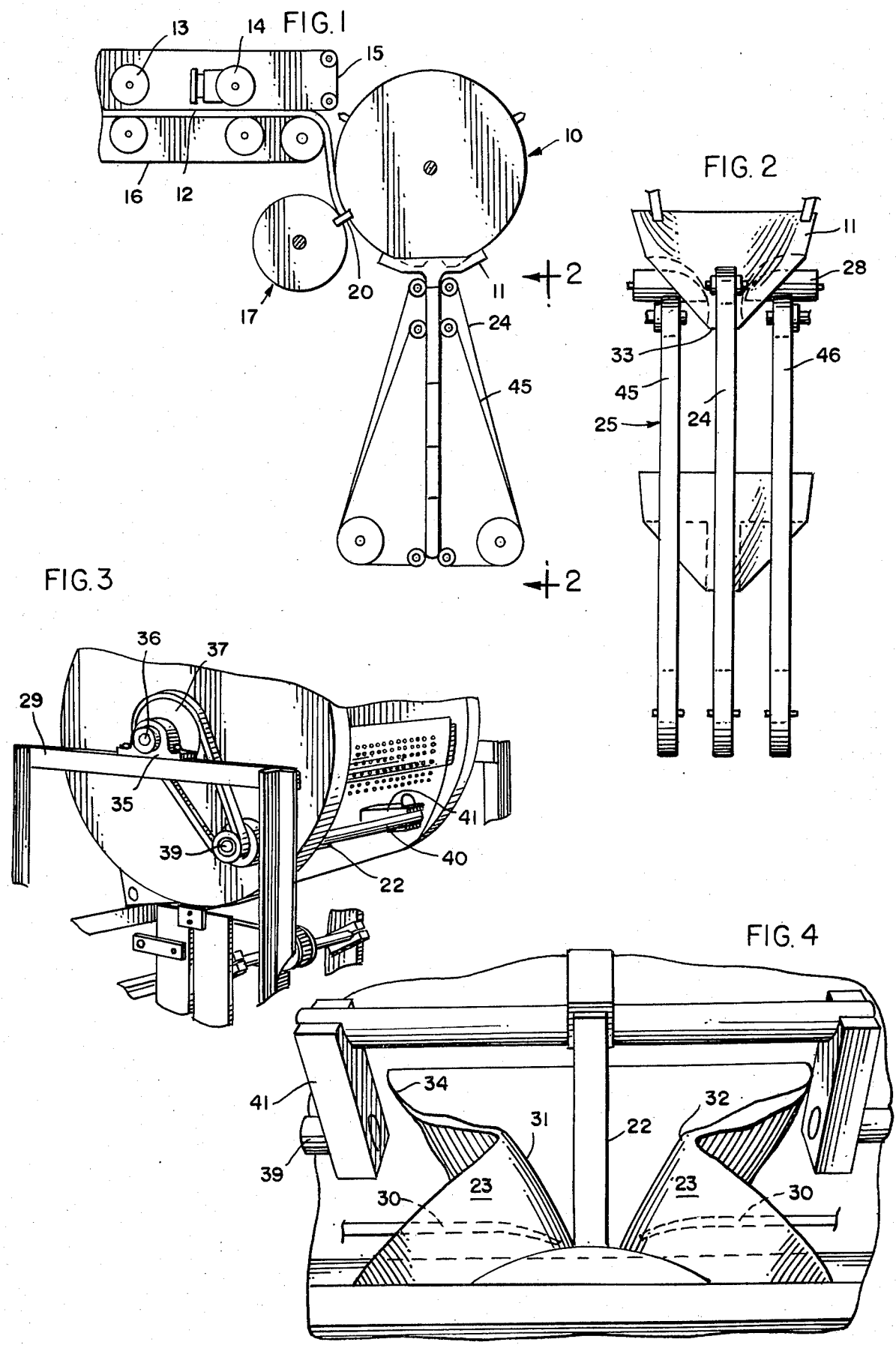

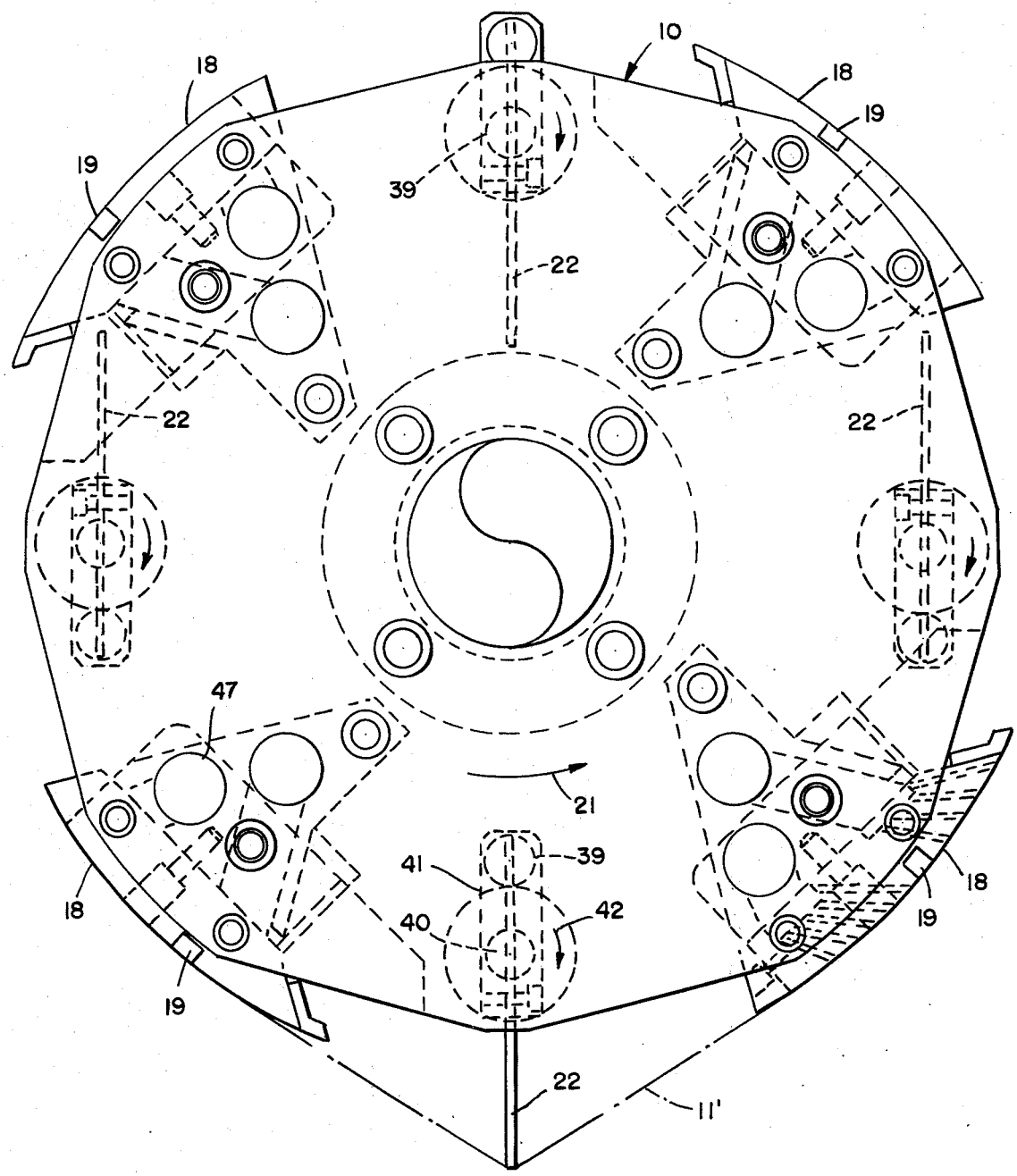

DIAPER FOLDING APPARATUS

This application is a continuation-in-part of my application Ser. No. 404,037, filed Oct. 5, 1973, now U.S. Pat. No. 3,860,004 which in turn was a continuation-in-part of my co-pending applications Ser. No. 297,750 filed Oct. 16, 1972 and Ser. No. 373,247, filed June 25, 1973, now both abandoned.

This invention relates to apparatus for the folding of disposable diapers. Conventionally, disposable diapers are made on high speed machinery and consist of an outer web of moisture proof material such as polyethylene, an internal layer of wadding or fluff of great absorbency, and an inner (relative to the infant) layer of moisture permeable material such as a non-woven cellulosic material. These webs are united at high speed in a continuous fashion in an elongated machine, the output being the final folded diaper ready for packaging. By high speed, I refer to the fact that several hundred diapers can be produced each minute.

Most of the operations provided in diaper making machinery function with the web or webs traveling in a straight line at relatively high speed. It will be appreciated that the concept of folding departs from this, particularly when leg folds are introduced, i.e., approximating the diaper to the historical "three cornered" variety. Even though rotary mechanisms for introducing such folds (see, for example, U.S. Pat. No. 3,782,714) have been developed and utilized, it would be desirable to have a high speed simple, yet rugged folding device which operates in conjunction with the high speed diaper forming machine — and the provision of such is an important objective of this invention.

According to the invention, an open frame drum is employed which is rotated in the path of diapers issuing from the forming machine, the frame being equipped with a rapidly projecting or emerging tucker which thrusts an intermediate portion of the diaper into a takeaway belt system while the diaper is pulled over forming plates which develop the leg fold.

DETAILED DESCRIPTION OF INVENTION

The invention is described in conjunction with an illustrative embodiment in the accompanying drawing, in which FIG. 1 is a schematic elevational view of a portion of disposable diaper producing apparatus and which features the inventive folding device;

FIG. 2 is an end elevational view such as would be seen essentially along the line 2—2 applied to FIG. 1;

FIG. 3 is a fragmentary perspective (and partially schematic) view of the drum portion of the apparatus as seen in the upper right hand portion of FIG. 1;

FIG. 4 is a fragmentary perspective view looking into the drum of FIG. 3 generally along the sight line 4—4 of FIG. 3 but additionally showing a diaper in the process of being folded;

FIG. 6 is another fragmentary side elevational view of the folding drum and featuring the arrangement of vacuum heads for supporting edge portions of a diaper for folding.

Figure 5:
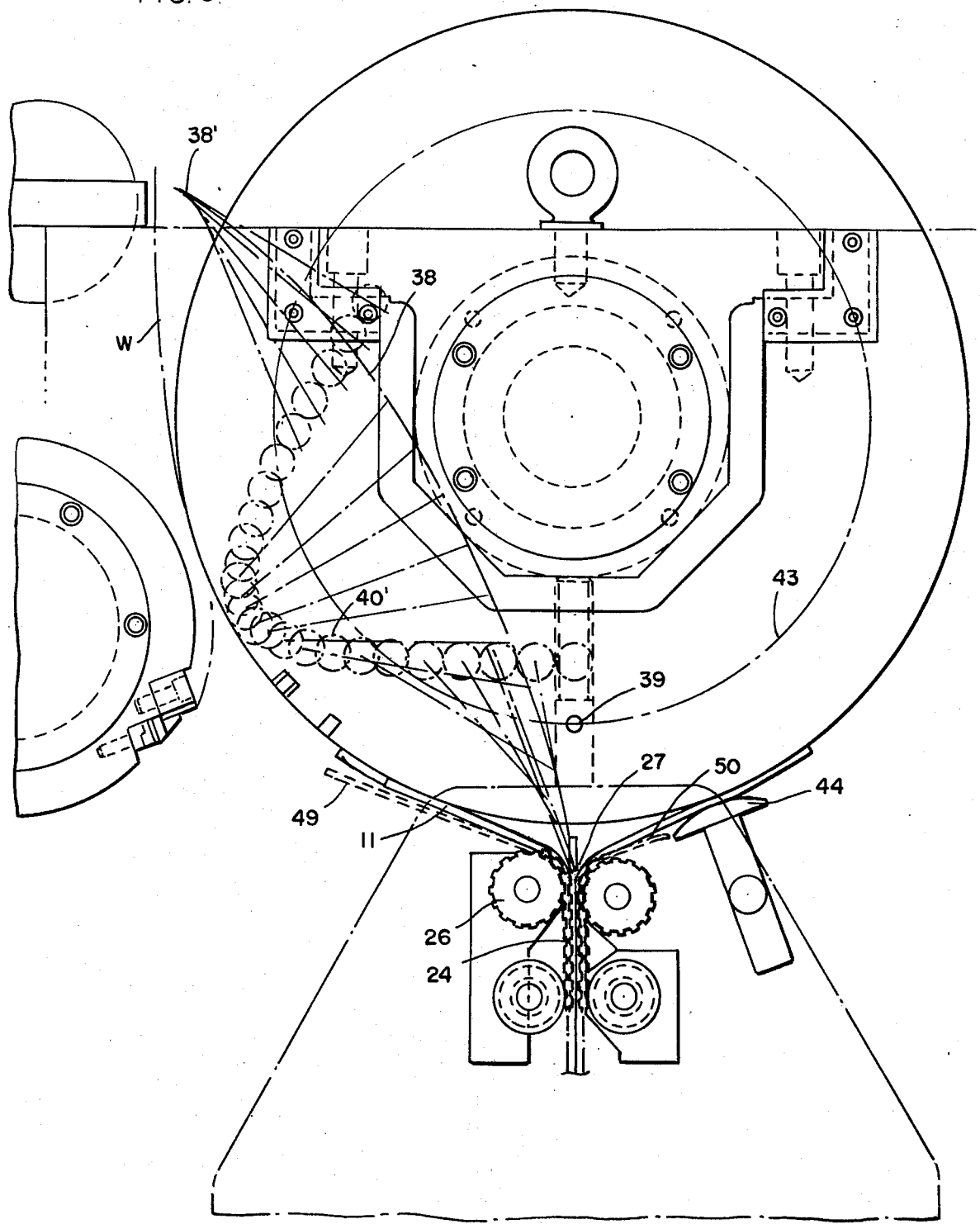
FIG. 5 is a fragmentary side elevational view of the folding apparatus of the invention and which shows in detail the path of movement of the tucker blade in achieving a fold.

In the illustration given, and with reference first to FIG. 1, the numeral 10 designates generally a folding drum which is seen in the process of folding a diaper 11 — see also the extreme upper portion of FIG. 2. Prior to the folding initiated by the drum 10, a web 12 of disposable diaper material, i.e., conventionally the polyethylene outer web, fluff or wadding core, and nonwoven inner layer, is advanced through scoring rolls 13 and an adhesive applicator roll 14 by means of belt systems 15 and 16. The web 12 is cut into discrete segments by a cutoff roll generally designated 17 and which coacts with the drum 10.

Referring, for the moment, to FIG. 6, the drum 10 is again seen and is equipped with a plurality of vacuum heads 18. Each anvil head 18 has, intermediate its length, an anvil 19 which coacts with a cutoff blade 20 mounted on the cutoff roll.

Still referring to FIG. 6, the drum 10 is a "4-time" roll in that each revolution of the drum will produce four diapers. The diaper previously referred to by the numeral 11 is represented schematically in FIG. 6 by the dashed line designated 11'. It will be seen that the diaper 11' extends between adjacent anvils 19 so thet the leading edge portion of the diaper 11' (or 11, as the case may be) is supported on one vacuum head while the trailing portion of the diaper is supported on the next following vacuum head 18 — the direction of the drum 10 in FIG. 6 being designated by the numeral 21.

It will be appreciated that the diaper web 12 is crosssealed at regular intervals, i.e., each 16 inches. Thus, the cutoff 20 engages an anvil every 16 inches to provide a stream of unfolded disposable diapers.

The commencement of the folding operation is best seen in FIG. 4 where a tucker 22 (see also the extreme lower portion of FIG. 6) engages an unsupported, intermediate portion of the diaper. Therefore, it is advantageous to provide a drum 10 of the open frame type wherein the tucker can be mounted internally and have adequate room to emerge rapidly and develop the partial transverse fold. By partial transverse fold, I refer to the fact that the tucker 22 is relatively narrow, i.e., of the order of 1 inch in width — as compared to the normal diaper width of 8 inches. The action of the tucker 22 on the diaper 11 develops a useful pocket or crotch in the diaper and sets the stage for the development of the leg folds 23 (designated only in FIG. 4).

The tucker 22 serves to introduce or thrust a central partially folded portion of the diaper 11 between the center pair of belts 24 of the belt takeaway system generally designated 25. A diaper 11 in this orientation can be seen in the lower central portion of FIG. 5. I find it useful to employ a cog or ribbed belts for this purpose, and training the same over cog wheels as at 26 (see FIG. 5).

At the same time that the central, partial fold in the diaper is being urged by the tucker 22 into the nip 27 between the belts 24, the portions of the diaper 11 lateral of this central transverse fold are forced over forming plates 28 (see particularly FIG. 2). The forming plates are essentially planar and are disposed on the machine frame 29 (see FIG. 3) in aligned, spaced apart relation so as to accommodate the entry therebetween of the tucker 22.

I have found it advantageous to provide an "air assist" to the development of the leg folds 23. For this purpose, the planar plates 28 are hollow and equipped with air jet apertures as at 30 (see FIG. 4) which provides timed air jets. Thus, at the time the diaper is passing downwardly (compare FIGS. 2 and 4), the air jets are actuated so as to force lateral portions (relative to the portion contacted by the tucker 22) upwardly to form a pair of infolds 31 and 32 (see FIG. 4) on each side of and aligned with the partial outfold 33 (see FIG. 2) which represents the pocket of the diaper. At the same time angularly developed outfolds as at 34 (see FIG. 4) are developed in the diaper. It will be appreciated that the mechanical elements just described constitute a simple, but extremely rugged and reliable system for folding diapers at high speed. The elements perform in a rotary manner and readily accessible for repair, if necessary, and quick ascertaining of any fault.

Referring now to FIG. 3, it will be seen that the drum 10 is also mounted on a portion of the machine frame 29 via suitable bearings as at 35. The axle 36 of the drum 10 is suitably driven by a motor (not shown) in synchronism with the belt systems 15 and 16 (see FIG. 1) so as to develop the same surface speed as the linear rate of travel as the web 12. To power the tuckers 22 (and with a 4-time drum 10, as seen in FIG. 6 four tuckers are required), a belt and pulley system generally designated 37 (see FIG. 3) is provided. For simplicity of illustration and ease of understanding, I have shown the drive for only one tucker. The tucker arrangement I prefer is of the epicyclic type to provide a pattern of tucker-tip movement such as that designated by the numeral 38 in FIG. 5. To achieve this, I provide each tucker assembly with a cross shaft 39 (see FIGS. 3–6) which is driven by the belt system 37. The tucker blade 11 as can be best seen in FIGS. 3 and 4, is mounted on a cross bar 40 which in turn is mounted eccentrically relative to the stub shafts 39 by means of crank arms 41 (best seen in FIG. 4). In the illustration given, each tucker rotates at twice the speed of the drum 10 and in the opposite direction, i.e., clockwise as at 42 (see the bottom portion of FIG. 6) as contrasted to the clockwise rotation of the drum as seen by the arrow 21. For example, and with reference to FIG. 6, the uppermost tucker 22, i.e., the one in the 12 o'clock position, is seen to be disposed radially inwardly, i.e., straight down. By the time the drum has made one quarter rotation — so as to bring the tucker 22 to the 9 o'clock position, the tucker blade 22 has swept through 180° and is now pointing straight up. Therefore, during this rotation, the tucker blade 22 has, when it is positioned half-way between the 12 o'clock and 9 o'clock position, assumed an orientation where it is directed radially outwardly and this is the extreme upper end of the pattern designated 38 in FIG. 5, i.e., as at 38'.

Thereafter, as the drum 10 continues to rotate in a counterclockwise fashion, the stub shafts 39 follow the circular path 43 indicated in FIG. 5. However, the cross shaft 40 follows an epicyclic path as shown by the sequence of circles in the left hand portion of the drum 10 in FIG. 5. This causes the tucker blade to sweep through the path 38 from one point of issuance 38' to the bottom position in FIG. 5 wherein the tucker is engaged in the folding operation. The various dispositions of the tucker blade 22 are shown in dashed line from the various circles 40' to the envelope line 38. This particular type of motion is quite satisfactory for tucking in that there is a relatively quick protrusion of the tucker, i.e, a small rotational movement of the drum results in a substantial change of attitude of the tucker blade, i.e., characteristic of the "cusp" associated with epicyclic movement.

I have further found it advantageous to provide means in the form of the sector roll 44 (see FIG. 5) for controlling one of the edge portions of the diaper 11 against displacement upon engagement of the diaper by the tucker 22. This insures that each diaper will be transversely folded at the same position. It will be appreciated that the diaper is initially held in conformity with the exterior of the drum, i.e., against the vacuum heads 18 and that as the tucker 22 emerges, the diaper must slide relative to one or both of the vacuum heads 18 in order to accommodate the tucking action. By controlling the leading edge of the diaper, only the trailing edge of the diaper slides relative to its associated vacuum head 18 until released by sector roll 44. This, then insures that each successive diaper will be folded at precisely the same position longitudinally of the diaper. As with the drum 10, the sector roll 44 is rotatably supported on the frame 29 and is driven in synchronism with the drum 10 through suitable gearing (not shown). The same is true of the belt system 25, i.e., being driven in synchronism with the remainder of the folding apparatus. From a consideration of FIGS. 1 and 2, it will be seen that side belts 45 and 46 are provided in addition to the belts 24, these being foreshortened at the upper end of the run to accommodate the forming plates 28.

Omitted, for the sake of clarity, is the vacuum manifold or valve which is essentially a crescent-shaped device mounted on the frame 29 and disposed about the lower portion of the drum 10, i.e., so as to come into communication with the vacuum passage 47 (see the lower left hand portion of FIG. 6) at about the time when the associated vacuum head 18 is in the 9 o'clock position. This permits the drum 10 to pick up the web W when it comes into tangency as seen in the upper left hand portion of FIG. 5.

I also find it advantageous to provide shields or guides 49 and 50 (see the lower portion of FIG. 5), aligned with the path of movement of the tucker 22. Particularly, the guide 50 fits into the space between the aligned forming plates 28 and prevents premature gripping of the partially folded diaper by the belts 24. The shields 49 and 50 are also supported on the frame 29.

I claim:

1. Apparatus for folding disposable diapers comprising a frame, means operably associated with said frame for advancing unfolded disposable diapers along a predetermined path whereby each diaper has leading and trailing edge portions.

a drum mounted on said frame in the path of diaper advancement, said frame being equipped with means for rotating said drum about its axis and with further means for applying suction to circumferentially spaced apart areas of the periphery of said drum for holding said leading and trailing edge portions of the diaper against the drum, said drum having an opening in the periphery thereof between said circumferentially spaced apart areas and confronting the portion of said diaper between said leading and trailing edge portions, a tucker mounted in said drum for rapid projection from said drum against said diaper confronting portion to develop a transverse outfold in said diaper, a pair of wheels rotatably mounted in side-by-side spaced relation on said frame adjacent said drum in axially aligned relation thereto and positioned adjacent a point in said path where said tucker projects from said drum whereby said tucker is adapted to project said diaper confronting portion between said wheels for takeaway from said drum, a pair of aligned, spaced apart generally planar folding plates mounted on said frame extending generally radially of said drum and positioned along a plane passing between said wheels so as to also be positioned adjacent a point in said path where said tucker projects from said drum, the spacing of said plates permitting said tucker to project between said plates in developing said transverse outfold, said plates opposing the development of an outfold extending the full diaper width but instead forming an infold in each diaper aligned with the partially developed outfold and on each side thereof, each plate being equipped with an inwardly directed air jet, and a belt system for gripping a diaper to move the same generally radially away from said drum while said diaper infolds are passing over said plates.

2. The structure of claim 1 in which said frame is equipped with further means for controlling one of said leading and trailing edge portions against displacement upon engagement of a diaper by said tucker.

3. The structure of claim 1 in which said folding plates are each equipped with timed air jets directed inwardly of said drum for assisting in developing of said infolds.

4. The structure of claim 1 in which a plurality of tuckers are mounted in said drum, each of said tuckers being mounted for epicyclic movement.

5. The structure of claim 1 in which said frame is equipped with guides to prevent premature engagement of said belt system with a diaper in the process of being folded, said guide being mounted in alignment with the space between said folding plates and with one of said guides projecting toward said belt system.

* * * * *